(12) United States Patent
Evans et al.

(10) Patent No.: US 7,348,444 B2
(45) Date of Patent: Mar. 25, 2008

(54) PROCESS FOR THE PRODUCTION OF AN OLEFIN OXIDE

(75) Inventors: Wayne Errol Evans, Richmond, TX (US); Marek Matusz, Houston, TX (US)

(73) Assignee: Shell Oil Company, Houston, TX (US)

( * ) Notice: Subject to any disclaimer, the term of this patent is extended or adjusted under 35 U.S.C. 154(b) by 29 days.

(21) Appl. No.: 10/816,480

(22) Filed: Apr. 1, 2004

(65) Prior Publication Data

US 2004/0236124 A1    Nov. 25, 2004

Related U.S. Application Data

(60) Provisional application No. 60/460,901, filed on Apr. 7, 2003.

(51) Int. Cl.
*C07D 323/02* (2006.01)
*C07D 317/44* (2006.01)
*B01J 20/34* (2006.01)
*B01J 23/60* (2006.01)

(52) U.S. Cl. ............... 549/534; 549/534; 549/536; 502/51; 502/347

(58) Field of Classification Search ............ 549/534, 549/536; 502/51, 397
See application file for complete search history.

(56) References Cited

U.S. PATENT DOCUMENTS

| | | | |
|---|---|---|---|
| 2,219,575 A | 10/1940 | McNamee et al. | 260/348 |
| 4,007,135 A | 2/1977 | Hayden et al. | 252/467 |
| 4,389,338 A | 6/1983 | Mitsuhata et al. | 252/463 |
| 4,400,559 A | 8/1983 | Bhise | 568/858 |
| 4,761,394 A | 8/1988 | Lauritzen | 502/348 |
| 4,766,105 A | 8/1988 | Lauritzen | 502/216 |
| 4,822,900 A | 4/1989 | Hayden | 549/534 |
| 4,845,296 A | 7/1989 | Ahmed et al. | 564/477 |
| 4,874,879 A | 10/1989 | Lauritzen et al. | 549/536 |
| 5,100,859 A | 3/1992 | Gerdes et al. | 502/439 |
| 5,102,848 A | 4/1992 | Soo et al. | 502/218 |
| 5,155,242 A | 10/1992 | Shankar et al. | 549/534 |
| 5,380,697 A | 1/1995 | Matusz et al. | 502/348 |
| 5,395,812 A | 3/1995 | Nagase et al. | 502/238 |
| 5,407,888 A | 4/1995 | Herzog et al. | 502/317 |
| 5,444,034 A | 8/1995 | Rizkalla | 502/347 |
| 5,504,052 A | 4/1996 | Rizkalla et al. | 502/347 |
| 5,646,087 A | 7/1997 | Rizkalla et al. | 502/347 |
| 5,736,483 A | 4/1998 | Rizkalla | 502/347 |
| 5,739,075 A | 4/1998 | Matusz | 502/302 |
| 5,770,746 A | 6/1998 | Cooker et al. | 549/534 |
| 5,780,656 A | 7/1998 | Rizkalla et al. | 549/534 |
| 5,801,259 A | 9/1998 | Kowaleski | |
| 5,854,167 A | 12/1998 | Rizkalla et al. | 502/216 |
| 5,905,161 A * | 5/1999 | Boeck et al. | 549/534 |
| 6,087,299 A | 7/2000 | Grub et al. | 502/347 |
| 6,368,998 B1 | 4/2002 | Lockemeyer | 502/347 |
| 6,372,925 B1 * | 4/2002 | Evans et al. | 549/536 |
| 6,511,938 B1 | 1/2003 | Liu et al. | 502/347 |
| 6,518,441 B2 * | 2/2003 | Grosch et al. | 549/531 |
| 6,579,825 B2 | 6/2003 | Lockemeyer | 502/347 |
| 6,656,874 B2 | 12/2003 | Lockemeyer | 502/347 |
| 6,750,173 B2 | 6/2004 | Rizkalla et al. | 502/348 |
| 6,762,311 B2 | 7/2004 | Rizkalla et al. | 549/534 |
| 7,102,022 B2 | 9/2006 | Evans et al. | 549/536 |
| 2002/0010094 A1 | 1/2002 | Lockemeyer | 502/439 |

FOREIGN PATENT DOCUMENTS

| | | |
|---|---|---|
| EP | 003642 A2 | 8/1979 |
| EP | 266015 A1 | 5/1988 |
| EP | 326392 A1 | 8/1989 |
| EP | 352849 A1 | 1/1990 |
| EP | 352850 | 1/1990 |
| EP | 211521 | 3/1990 |
| EP | 0448157 | 9/1991 |
| EP | 567273 A1 | 10/1993 |
| EP | 716884 A2 | 6/1996 |
| EP | 933130 A2 | 8/1999 |
| EP | 1002575 A2 | 5/2000 |
| GB | 1170663 | 11/1969 |
| GB | 1191983 | 5/1970 |
| GB | 1489335 | 10/1977 |
| SU | 1572414 | 6/1990 |
| WO | 95/05896 | 3/1995 |
| WO | 95/17957 | 7/1995 |
| WO | 96/04989 A1 | 2/1998 |
| WO | 00/15332 | 3/2000 |
| WO | 00/15333 | 3/2000 |

(Continued)

OTHER PUBLICATIONS

Kirk-Othmer's Encyclopedia Of Chem. Tech., 3$^{rd}$ Ed., vol. 9 (1980), pp. 445-447.

(Continued)

*Primary Examiner*—Janet L. Andres
*Assistant Examiner*—Raymond Covington

(57) ABSTRACT

A process for the production of an olefin oxide, which process comprises reacting a feed comprising an olefin and oxygen in the presence of a silver-containing catalyst, wherein before the catalyst has reached an advanced stage of ageing the reaction temperature is above 255° C. and the olefin content of the feed is above 25 mole-%, relative to the total feed.

13 Claims, No Drawings

FOREIGN PATENT DOCUMENTS

| WO | 00/15334 | 3/2000 |
|---|---|---|
| WO | 00/15335 | 3/2000 |
| WO | WO 01/96324 | 12/2001 |
| WO | 2004/002972 A2 | 1/2004 |

OTHER PUBLICATIONS

Kirk-Othmer's Encyclopedia Of Chem. Tech., 2nd Ed., vol. 4 (1964), p. 566.

Brunauer, Emmet & Teller, J. of Amer. Chem. Soc., vol. 60 (1938); pp. 309-316.

Beilstein Institute for Organic Chemistry, Frankfurt-Main, DE, XP002296657, J. Am. Chem. Soc., vol. 56 (1934); pp. 1870-1872.

International Search Report, dated Jan. 18, 2005, for PCT/US2004/010457 (TH2467 PCT).

International Preliminary Examination Report, dated Aug. 18, 2005, for PCT/US2004/010457 (TH2467 PCT).

International Search Report, dated Jun. 11, 2004, for PCT/US03/19827 (TH1808 PCT).

International Search Report, dated Feb. 20, 2004, for PCT/US03/20095 (TH2202 PCT).

International Search Report, dated Oct. 30, 2003, for PCT/US2003/019828 (TH2305 PCT).

Letter to European Patent Office date Jul. 11, 2000, relating to European Patent Application No. 95203469.2-2104, Publication No. 716884.

U.S. Patent and Trademark Office Action for U.S. Appl. No. 10/606,440 (TH1808) dated Feb. 25, 2005.

U.S. Patent and Trademark Office Action for U.S. Appl. No. 10/606,440 (TH1808) dated Aug. 18, 2005.

International Preliminary Examination Report, dated Oct. 27, 2004, for PCT/US2003/19827 (TH1808 PCT).

International Preliminary Examination Report, dated Oct. 5, 2004, for PCT/US2003/20095 (TH2202 PCT).

International Preliminary Examination Report, dated Oct. 29, 2004, for PCT/US2003/19828 (TH2305 PCT).

Written Opinion, dated Jul. 16, 2004, for PCT/US03/19827 (TH1808 PCT).

Written Opinion, dated Mar. 16, 2004, for PCT/US03/20095 (TH2202 PCT).

Written Opinion, dated May 6, 2005, for PCT/US03/19828 (TH2305 PCT).

* cited by examiner

PROCESS FOR THE PRODUCTION OF AN OLEFIN OXIDE

This application claims the benefit of U.S. Provisional Application Ser. No. 60/460,901 filed Apr. 7, 2003, the entire disclosure of which is hereby incorporated by reference.

FIELD OF THE INVENTION

The present invention relates to a process for the production of an olefin oxide, a 1,2-diol, a 1,2-diol ether or an alkanolamine.

BACKGROUND OF THE INVENTION

In olefin epoxidation an olefin is reacted with oxygen to form an olefin epoxide, using a catalyst comprising a silver component, usually with one or more further elements deposited therewith on a support. The olefin oxide may be reacted with water, an alcohol or an amine to form a 1,2-diol, a 1,2-diol ether or an alkanolamine. Thus, 1,2-diols, 1,2-diol ethers and alkanolamines may be produced in a multi-step process comprising olefin epoxidation and converting the formed olefin oxide with water, an alcohol or an amine.

The performance of the epoxidation process may be assessed on the basis of the selectivity, the catalyst's activity and stability of operation. The selectivity is the molar fraction of the converted olefin yielding the desired olefin oxide. The catalyst is subject to an ageing-related performance decline during normal operation. The ageing manifests itself by a reduction in the activity of the catalyst. Usually, when a reduction in activity of the catalyst is manifest, the reaction temperature is increased in order to compensate for the reduction in activity, however at the expense of selectivity. In the typical operation of a fresh catalyst, the process is operated at a reaction temperature of at most 255° C. Upon catalyst ageing the reaction temperature may gradually be increased to values substantially above 255° C. until the reaction temperature becomes undesirably high, at which point in time the catalyst is deemed to be at the end of its lifetime and would need to be exchanged. It goes without saying that from an economical point of view it is highly desirable to improve the performance of the catalyst and to extend its lifetime as much as possible. Quite modest improvements in the maintenance of selectivity over long periods yields huge dividends in terms of efficiency in the olefin epoxidation process and, if applicable, also in the overall process for the production of a 1,2-diol, a 1,2-diol ether or an alkanolamine.

Therefore, for decades much research has been devoted to improving the activity, the selectivity and the lifetime of the catalysts, and to find process conditions which enable to fully exploit the catalyst performance.

An organic halide, for example a chlorohydrocarbon, may be added to the feed to an epoxidation reactor as a reaction modifier for increasing the selectivity. The reaction modifier suppresses the undesirable oxidation of olefin or olefin oxide to carbon dioxide and water, relative to the desired formation of olefin oxide.

U.S. Pat. No. 4,766,105 and U.S. Pat. No. 4,761,394 disclose that rhenium may be employed as a further element in the silver-containing catalyst with the effect that the selectivity of the olefin epoxidation is increased.

U.S. Pat. No. 6,372,925 and WO-01/96324 teach that when operating with a catalyst which exhibits an improved selectivity, for example a catalyst known from U.S. Pat. No. 4,766,105 or U.S. Pat. No. 4,761,394, it is advantageous to increase the ethylene content of the feed when the catalyst has reached a certain stage of ageing. The increased ethylene content substantially improves the selectivity of the conversion of ethylene into ethylene oxide.

Not withstanding the improvements already achieved, there is a desire to further improve the performance of the silver-containing catalysts in the production of the production of an olefin oxide, a 1,2-diol, a 1,2-diol ether or an alkanolamine.

SUMMARY OF THE INVENTION

The present invention provides a process for the production of an olefin oxide, which process comprises reacting a feed comprising an olefin and oxygen in the presence of a supported silver-containing catalyst, wherein before the catalyst has reached an advanced stage of ageing the reaction temperature is above 255° C. and the olefin content of the feed is above 25 mole-%, relative to the total feed.

The invention also provides a process for the production of an olefin oxide, which process comprises reacting a feed comprising an olefin and oxygen at a reaction temperature above 255° C. and an olefin content of the feed above 25 mole-%, relative to the total feed, in the presence of a silver-containing catalyst which has not reached an advanced stage of ageing.

The invention also provides a method of using an olefin oxide for making a 1,2-diol, a 1,2-diol ether or an alkanolamine comprising converting the olefin oxide into the 1,2-diol, the 1,2-diol ether or the alkanolamine, wherein the olefin oxide has been obtained by the process according to this invention.

DETAILED DESCRIPTION OF THE INVENTION

In accordance with this invention, when a fresh catalyst is used at a relatively high temperature, i.e. above 255° C., the performance of the catalyst, in particular the activity, the selectivity, and the ageing related performance decline, are improved when the olefin content of the feed is increased. Such improvements have not become apparent when the catalyst was used at a relatively low temperature.

This is unobvious over the teachings of U.S. Pat. No. 6,372,925 and WO-01/96324. These documents show the performance of fresh catalysts at their typical use temperature of at most 255° C. and the performance of aged catalysts at their typical use temperature of above 255° C. These documents are silent about the performance of fresh catalysts at reaction temperatures above 255° C.

As used herein, "an advanced stage of ageing" of the catalyst is defined by a cumulative olefin oxide production of at least 10,000 kmole, in particular at least 5000 kmole, more in particular at least 2000 kmole, most in particular at least 1000 kmole, of olefin oxide per $m^3$ of catalyst bed. As used herein, "fresh catalyst" means a catalyst immediately after its preparation or rejuvenation, or a catalyst which, in the course of operation, has not yet reached an advanced stage of ageing.

Although the present epoxidation process may be carried out in many ways, it is preferred to carry it out as a gas phase process, i.e. a process in which the feed is contacted in the gas phase with the catalyst which is present as a solid material, typically in a packed bed. Generally the process is carried out as a continuous process.

The olefin for use in the present epoxidation process may be any olefin, such as an aromatic olefin, for example styrene, or a di-olefin, whether conjugated or not, for example 1,9-decadiene or 1,3-butadiene. Typically, the olefin is a monoolefin, for example 2-butene or isobutene. Preferably, the olefin is a mono-α-olefin, for example 1-butene or propylene. The most preferred olefin is ethylene.

The olefin content of the feed is above 25 mole-%, typically at least 30 mole-%, more typically at least 35 mole-%, relative to the total feed. Typically the olefin content of the feed is at most 80 mole-%, more typically at most 70 mole-%, relative to the total feed. In preferred embodiments, amongst others, the olefin content of the feed is maintained at a value of at least 25 mole-%, typically at least 30 mole-%, more typically at least 35 mole-%, relative to the total feed, when the catalyst has reached an advanced stage as ageing. Also at an advanced stage of ageing the olefin content of the feed is typically at most 80 mole-%, more typically at most 70 mole-%, relative to the total feed. Typically the olefin content of the feed is maintained at the value as defined for at least a period which is sufficient to effect an olefin oxide production of at least 1000 kmole, more typically at least 5000 kmole, most typically at least 10,000 kmole, of olefin oxide per $m^3$ catalyst bed, preferably up to the end of the catalyst's lifetime, that is when the catalyst will be exchanged and/or rejuvenated. As used herein, the feed is considered to be the composition which is contacted with the catalyst.

The direct oxidation of an olefin to the corresponding olefin oxide can be air-based or oxygen-based, see Kirk-Othmer's *Encyclopedia of Chemical Technology*, 3rd ed., Vol. 9 (1980) p. 445–447. In the air-based processes air or air enriched with oxygen is fed directly to the system while in the oxygen-based processes high-purity (above 95 mol-%) oxygen is employed as the source of the oxidizing agent. Presently most ethylene oxide production plants are oxygen-based and this is the preferred embodiment of the present invention.

The oxygen content of the feed is within the broad range of from 3 to 20 mole-%, preferably from 5 to 12 mole-%, relative to the total feed.

In order to remain outside the flammability limit of the reaction mixture, the oxygen content of the feed is usually balanced with the olefin content. The actual safe operating ranges depend, along with the gas composition (reactants and balance gases), also on individual plant conditions such as temperature and pressure.

In addition to the olefin and oxygen, the feed may contain one or more optional components, such as carbon dioxide, a reaction modifier and balance inert gases.

Carbon dioxide is a by-product of the olefin oxidation process. Since frequently unconverted olefin is continuously recycled, and since a content of carbon dioxide in the feed which is much in excess of 15 mole-% will have an adverse effect on catalyst activity, accumulation of carbon dioxide will be avoided by continuously removing carbon dioxide from the recycle gas. This may be done by venting and by continuous absorption of the formed carbon dioxide. Currently contents of carbon dioxide as low as 1 mole-% are practical, for example in the range of from 0.5 to 1 mole-%, and in future even lower contents may be reached. The process of the present invention is independent of the presence or absence of carbon dioxide in the reaction mixture.

A reaction modifier may be added to the feed for increasing the selectivity, suppressing the undesirable oxidation of olefin and of the olefin oxide to carbon dioxide and water. Many organic compounds, especially organic halides but also amines, organometallic compounds and aromatic hydrocarbons are known to be effective in this respect. Organic halides are the preferred reaction modifiers and they are effective without suppressing the desired reaction when used in quantities ranging from 0.1 to 25 parts per million by volume (ppmv), in particular from 0.3 to 20 ppmv, relative to the total feed. Dependent of the silver-containing catalyst employed, the reaction modifier content of the feed may be optimized from time to time during operation if the maximum achievable selectivity is to be maintained. Preferred organic halides are $C_1$ to $C_8$ chlorohydrocarbons or bromohydrocarbons. More preferably they are selected from the group of methyl chloride, ethyl chloride, ethylene dichloride, ethylene dibromide, vinyl chloride or a mixture thereof. Most preferred reaction modifiers are ethyl chloride and ethylene dichloride.

The balance inert gases usually present in the feed comprise, for example, nitrogen, argon, and/or saturated hydrocarbon such as methane or ethane. When unconverted olefin is continuously recycled, and oxygen added, the accumulation of balance gases is avoided. The process of the present invention is independent of the amount of balance inert gases in the reaction mixture.

"GHSV", or Gas Hourly Space Velocity, is the unit volume of gas at standard temperature and pressure (0° C., 1 atm, i.e. 101.3 kPa) passing over one unit volume of packed catalyst per hour. Preferably, if the process is carried out as a gas phase process, the GHSV is in the range of from 1500 to 10000. The reactor inlet pressure is preferably in the range of from 1000 to 3500 kPa.

The reaction temperature is typically at least 260° C., more typically at least 265° C., most typically at least 270° C. The reaction temperature is typically at most 325° C., more typically at most 310° C. In preferred embodiments, amongst others, the reaction temperature is maintained at a value of above 255° C., typically at least 260° C., more typically at least 265° C., most typically at least 270° C. when the catalyst has reached an advanced stage of ageing. Also at an advanced stage of ageing the reaction temperature is typically at most 325° C., more typically at most 310° C. Typically the reaction temperature is maintained at the value as defined for at least a period which is sufficient to effect an olefin oxide production of at least 1000 kmole, more typically at least 5000 kmole, most typically at least 10,000 kmole, of olefin oxide per $m^3$ catalyst bed, preferably up to the end of the catalyst's lifetime, that is when the catalyst will be exchanged and/or rejuvenated.

The present process may be started-up by using procedures known in the art, for example from U.S. Pat. No. 4,874,879, and U.S. Pat. No. 5,155,242, which are incorporated herein by reference. After passing the start-up phase, and at some point in time before the catalyst has reached an advanced stage of ageing, the catalyst may be subjected to the conditions of reaction temperature and olefin content of the feed as defined in accordance with this invention, until the catalyst has reached an advanced stage of ageing. In this context, the stage of ageing of the catalyst is considered on the basis of the total quantity of olefin oxide produced, that is including for example the olefin oxide production, if any, during the start-up procedure.

The material of the support of the supported silver-containing catalysts may be selected from a wide range of conventional materials which are considered to be inert in the presence of the olefin oxidation feed, products and reaction conditions. Such conventional materials can be natural or artificial and they may include aluminum oxides, magnesia, zirconia, silica, silicon carbide, clays, pumice, zeolites and charcoal. Alpha alumina is the most preferred material for use as the main ingredient of the porous support.

The support is typically porous and has preferably a surface area, as measured by the B.E.T. method, of less than 20 m$^2$/g and more in particular from 0.05 to 20 m$^2$/g. Preferably the B.E.T. surface area of the support is in the range of 0.1 to 10, more preferably from 0.1 to 3.0 m$^2$/g. The B.E.T. method of measuring the surface area has been described in detail by Brunauer, Emmet and Teller in *J. Am. Chem. Soc.* 60 (1938) 309–316.

The catalyst comprises silver as a catalytically active metal. Appreciable catalytic activity is obtained by employing a silver content of the catalyst of at least 10 g/kg, relative to the weight of the catalyst. Preferably, the catalyst comprises silver in a quantity of from 50 to 500 g/kg, more preferably from 100 to 400 g/kg, relative to the weight of the catalyst.

The catalyst preferably comprises, in addition to silver, a further element or compound thereof. Eligible further elements may be selected from the group of nitrogen, sulfur, phosphorus, boron, fluorine, Group IA metals, Group IIA metals, rhenium, molybdenum, tungsten, chromium, titanium, hafnium, zirconium, vanadium, thallium, thorium, tantalum, niobium, gallium and germanium and mixtures thereof. Preferably the Group IA metals are selected from lithium, potassium, rubidium and cesium. Most preferably the Group IA metal is lithium, potassium and/or cesium. Preferably the Group IIA metals are selected from calcium and barium. Typically, the further element is present in the catalyst in a quantity of from 0.01 to 500 mmole/kg, more typically from 0.05 to 100 mmole/kg, calculated as the element on the total catalyst. Where possible, the further element may suitably be provided as an oxyanion, for example, as a perrhenate, sulfate, nitrate, nitrite, borate or molybdate, in salt or acid form. Salts of Group IA metals or Group IIA metals are suitable.

Preferably, the silver-containing catalyst is one which, when operated fresh, exhibits at 260° C. a theoretical selectivity at zero oxygen conversion, $S_0$, of at least 6/7 or 85.7 mole-%, more preferably 88 mole-%, most preferably 89 mole-%. The value of $S_0$ for a given catalyst is found by operating the catalyst at 260° C. in a range of oxygen conversions, resulting in a range of selectivity values S corresponding to the range of oxygen conversions. These values S are then extrapolated back to the theoretical value of S at zero oxygen conversion, by the use of conventional curve-fitting algorithms.

Preferred supported highly selective silver-containing catalysts to be used in the present invention are rhenium-containing catalysts. Such catalysts are known from U.S. Pat. No. 4,766,105 and U.S. Pat. No. 4,761,394, which are incorporated herein by reference. Broadly, these catalysts contain a catalytically effective amount of silver, a promoting amount of rhenium or compound thereof, a promoting amount of at least one further metal or compound thereof and optionally a co-promoting amount of a rhenium co-promoter selected from tungsten, molybdenum, chromium, sulfur, phosphorus, boron, and compounds thereof. More specifically the at least one further metal of these rhenium-containing catalysts is/are selected from the group of Group IA metals, Group IIA metals, titanium, hafnium, zirconium, vanadium, thallium, thorium, tantalum, niobium, gallium and germanium and mixtures thereof. Preferably the at least one further metal is/are selected from the Group IA metals such as lithium, potassium, rubidium and cesium and/or from the Group IIA metals such as calcium and barium. Most preferably it is lithium, potassium and/or cesium.

Preferred amounts of the components of these rhenium-containing catalysts are, when calculated as the element on the total catalyst:

silver from 10 to 500 g/kg, more preferably from 10 to 400 g/kg,
rhenium from 0.01 to 50 mmol/kg,
further metal or metals from 10 to 3000 mg/kg, and
optional rhenium co-promoter from 0.1 to 10 mmol/kg.

More preferably, the rhenium content of these catalysts is at least 0.5 mmole/kg, in particular at least 1.0 mmole/kg, more in particular at least 1.5 mmole/kg, when calculated as the element on the total catalyst. More preferably, the rhenium content of these catalysts is at most 40 mmole/kg, when calculated as the element on the total catalyst. Alternatively, the rhenium content of these catalysts, expressed relative to the surface area of the support, is preferably at least 0.0005 mmole/m$^2$, in particular at least 0.001 mmole/m$^2$, more in particular at least 0.0015 mmole/m$^2$. Preferably the rhenium content of these catalysts is at most 0.1 mmole/m$^2$, more preferably at most 0.05 mmole/m$^2$, relative to the surface area of the support.

As used herein, the quantity of Group IA metal present in the catalysts is deemed to be the quantity in so far as it can be extracted from the catalysts with de-ionized water at 100° C. The extraction method involves extracting a 10-gram sample of the catalyst three times by heating it in 20 ml portions of de-ionized water for 5 minutes at 100° C. and determining in the combined extracts the relevant metals by using a known method, for example atomic absorption spectroscopy.

As used herein, the quantity of Group IIA metal present in the catalysts is deemed to the quantity in so far as it can be extracted from the catalysts with 10% w nitric acid in de-ionized water at 100° C. The extraction method involves extracting a 10-gram sample of the catalyst by boiling it with a 100 ml portion of 10% w nitric acid for 30 minutes (1 atm., i.e. 101.3 kPa) and determining in the combined extracts the relevant metals by using a known method, for example atomic absorption spectroscopy. Reference is made to U.S. Pat. No. 5,801,259, which is incorporated herein by reference.

The olefin oxide produced may be recovered by using methods known in the art, for example by absorbing the olefin oxide in water and optionally recovering the olefin oxide from the aqueous solution by distillation. At least a portion of the aqueous solution containing the olefin oxide may be applied in a subsequent process for converting the olefin oxide into a 1,2-diol, a 1,2-diol ether or an alkanolamine.

The olefin oxide produced in the epoxidation process may be converted into a 1,2-diol, into a 1,2-diol ether or into an alkanolamine.

The conversion into the 1,2-diol or the 1,2-diol ether may comprise, for example, reacting the olefin oxide with water, suitably using an acidic or a basic catalyst. For example, for making predominantly the 1,2-diol and less 1,2-diol ether, the olefin oxide may be reacted with a ten fold molar excess of water, in a liquid phase reaction in presence of an acid catalyst, e.g. 0.5–1.0% w sulfuric acid, based on the total reaction mixture, at 50–70° C. at 1 bar absolute, or in a gas phase reaction at 130–240° C. and 20–40 bar absolute, preferably in the absence of a catalyst. If the proportion of water is lowered the proportion of 1,2-diol ethers in the reaction mixture is increased. The 1,2-diol ethers thus produced may be a di-ether, tri-ether, tetra-ether or a subsequent ether. Alternative 1,2-diol ethers may be prepared by converting the olefin oxide with an alcohol, in particular a primary alcohol, such as methanol or ethanol, by replacing at least a portion of the water by the alcohol.

The conversion into the alkanolamine may comprise reacting the olefin oxide with an amine, such as ammonia, an alkyl amine or a dialkylamine. Anhydrous or aqueous ammonia may be used. Anhydrous ammonia is typically used to favour the production of monoalkanolamine. For methods applicable in the conversion of the olefin oxide into the alkanolamine, reference may be made to, for example U.S. Pat. No. 4,845,296, which is incorporated herein by reference.

The 1,2-diol and the 1,2-diol ether may be used in a large variety of industrial applications, for example in the fields of food, beverages, tobacco, cosmetics, thermoplastic polymers, curable resin systems, detergents, heat transfer systems, etc. The alkanolamine may be used, for example, in the treating ("sweetening") of natural gas.

Unless specified otherwise, the organic compounds mentioned herein, for example the olefins, 1,2-diols, 1,2-diol ethers, alkanolamines and organic halides, have typically at most 40 carbon atoms, more typically at most 20 carbon atoms, in particular at most 10 carbon atoms, more in particular at most 6 carbon atoms. As defined herein, ranges for numbers of carbon atoms (i.e. carbon number) include the numbers specified for the limits of the ranges.

Having generally described the invention, a further understanding may be obtained by reference to the following examples, which are provided for purposes of illustration only and are not intended to be limiting unless otherwise specified.

EXAMPLE 1–5

(Example 1 for Comparison, Examples 2–5 According to the Invention)

A catalyst as defined in U.S. Pat. No. 4,766,105, containing silver, rhenium and rhenium co-promoter and having in the fresh state a theoretical selectivity $S_0$ at 260° C. of 93%, was used to produce ethylene oxide from ethylene and oxygen. To do this, 2.1-g samples of the crushed catalyst (0.8–1.4 mm) were each loaded into a stainless steel U-shaped tube. The tube was immersed in a molten metal bath (heat medium) and the ends were connected to a as flow system. The flow rate of the feed was adjusted, to give a gas hourly space velocity of 15,200 Nl/(l.h), as calculated for uncrushed catalyst. The flow rate was 35.7 Nl/h. The inlet pressure was 1450 kPa.

The feed passed through the catalyst bed in a "once-through" operation consisted of ethylene, oxygen, 3 mole-% carbon dioxide, 2.0 to 6.0 ppmv ethyl chloride and balance nitrogen. In each Example different contents of olefin and oxygen were chosen, and such that the oxygen content was the maximum considered to be allowable avoiding conditions of flammability.

The initial reactor temperature was 225° C. and this was ramped up at a rate of 10° C. per hour to 245° C. and then adjusted so as to achieve a constant ethylene oxide content of 2 mole-% in the outlet stream. For each of the ethylene/oxygen contents combinations, the ethyl chloride content of the feed was varied to identify and then apply the level that provided the optimum selectivity.

The initial performance data of the catalyst (Table I) were obtained when the catalysts had been on stream for a total of at least 1–2 days. A lower reaction temperature needed to accomplish a certain ethylene oxide content in the outlet stream is indicative for a higher activity of the catalyst.

TABLE I

| Example | Ethylene in feed (mole-%) | Oxygen in feed (mole-%) | Selectivity (mole-%) | Activity (° C.) |
|---|---|---|---|---|
| 1 [1] | 25 | 8.3 | 85.5 | 290 |
| 2 [2] | 30 | 8.0 | 86 | 289 |
| 3 [2] | 35 | 7.6 | 87.5 | 283 |
| 4 [2] | 40 | 7.2 | 87.5 | 283 |
| 5 [2] | 45 | 6.8 | 88 | 280 |

[1] comparative
[2] invention

EXAMPLES 6–10 (for Comparison)

The procedure as outlined for Examples 1–5 was repeated, except that the gas hourly space velocity was 4,100 Nl/(l.h), as calculated for uncrushed catalyst, and that the flow rate was 9.6 Nl/h.

The initial performance data of the catalyst (Table II) were obtained when the catalysts had been on stream for a total of at least 1–2 days.

TABLE II

| Example | Ethylene in feed (mole-%) | Oxygen in feed (mole-%) | Selectivity (mole-%) | Activity (° C.) |
|---|---|---|---|---|
| 6 [1] | 25 | 8.3 | 90 | 250 |
| 7 [1] | 30 | 8.0 | 89.5 | 249 |
| 8 [1] | 35 | 7.6 | 90 | 250 |
| 9 [1] | 40 | 7.2 | 90.5 | 250 |
| 10 [1] | 45 | 6.8 | 90.5 | 251 |

[1] comparative

A comparison of Examples 2–5 (According to the Invention) with Comparative Example 1 shows that when the process is operated at a high temperature, i.e. above 255° C., the activity of the catalyst becomes progressively higher when the olefin content of the feed is progressively increased to values above 25 mole-%, despite the fact that the content of the other reactant in the feed, oxygen, is decreased. In addition, a gain in selectivity is achieved. Comparative Examples 6–10 show that a similar increase in activity is not seen when the process is operated at a lower temperature. Instead, the activity tends to decrease with increasing olefin content.

EXAMPLE 11 (According to the Invention)

The procedure as outlined for Examples 1–5 was repeated, except that the oxygen content of the feed was 8 mole-%, the gas hourly space velocity of 16,500 Nl/(l.h), as calculated for uncrushed catalyst, the flow rate was 38.6 Nl/h, and the ethylene oxide content in the outlet stream was 1.8 mole-%. Further, the decline in catalyst performance was measured over a time period providing a cumulative ethylene oxide (EO) production of 1800 kmole/m$^3$. Then the ethylene content in the feed was increased to 45 mole-%, with unchanged oxygen content, and again the decline in catalyst performance was measured over a time period providing a cumulative ethylene oxide production of 1800 kmole/m$^3$.

The results have been given in Table III.

Example 11 (according to the invention) shows that when the process is operated at a high temperature, i.e. above 255° C., the catalyst maintains it performance better as the olefin content in the feed is higher.

TABLE III

| Ethylene in feed (mole-%) | Selectivity (mole-%) | Activity (° C.) | Selectivity decline after 1800 kmole/m$^3$ EO production, (mole-%) | Activity decline after 1800 kmole/m$^3$ EO production, (° C.) |
|---|---|---|---|---|
| 30 | 86.5 | 278 | 1.5 | 10 |
| 45 | 88 | 270 | 0.5 | 0 |

What is claimed is:

1. A process for the production of an olefin oxide, which process comprises the steps of:
    reacting a feed comprising an olefin and oxygen in the presence of a silver-containing catalyst, wherein before the catalyst has reached an advanced stage of ageing, reaction conditions comprise a reaction temperature above 255° C. and an olefin content of the feed in the range of from above 25 mole-% to at most 80 mole-%, relative to the total feed; and
    maintaining the reaction conditions for at least a period of time which is sufficient to effect a cumulative olefin oxide production of at least 1000 kmole of olefin oxide per m$^3$ catalyst bed before the catalyst has reached an advanced stage of ageing.

2. A process as claimed in claim 1, wherein the olefin is ethylene.

3. A process as claimed in claim 1, wherein the olefin content of the feed is in the range of from 30 to 80 mole-%.

4. A process as claimed in claim 3, wherein the olefin content of the feed is in the range of from 35 to 70 mole-%.

5. A process as claimed in claim 1, wherein the olefin content of the feed is maintained at the value as defined for at least a period of time which is sufficient to effect an olefin oxide production of at least 5000 kmole of olefin oxide per m$^3$ catalyst bed before the catalyst has reached an advanced stage of ageing.

6. A process as claimed in claim 1, wherein the reaction temperature is in the range of from 260 to 325° C.

7. A process as claimed in claim 6, wherein the reaction temperature is in the range of from 270 to 310° C.

8. A process as claimed in claim 1, wherein the reaction temperature is maintained at the value as defined for at least a period of time which is sufficient to effect an olefin oxide production of at least 5000 kmole of olefin oxide per m$^3$ catalyst bed before the catalyst has reached an advanced stage of ageing.

9. A process as claimed in claim 1, wherein "an advanced stage of ageing" of the catalyst is defined by a cumulative olefin oxide production of at least 10,000 kmole of olefin oxide per m$^3$ of catalyst bed.

10. A process as claimed in claim 1, wherein "an advanced stage of ageing" of the catalyst is defined by a cumulative olefin oxide production of at least 2000 kmole of olefin oxide per m$^3$ of catalyst bed.

11. A process as claimed in claim 1, wherein the catalyst comprises, in addition to silver, rhenium or compound thereof, and a rhenium co-promoter selected from tungsten, molybdenum, chromium, sulfur, phosphorus, boron, and compounds thereof.

12. A method of using an olefin oxide for making a 1,2-diol, a 1,2-diol ether or an alkanolamine comprising converting the olefin oxide into the 1,2-diol, the 1,2-diol ether or the alkanolamine, wherein the olefin oxide has been obtained by a process as claimed in claim 1.

13. A process as claimed in claim 1, additionally comprising maintaining a reaction temperature of at most 325° C. and an olefin content of the feed of at most 80 mole-%, relative to the total feed, after the catalyst has reached an advanced stage of ageing.

* * * * *